(12) United States Patent
Ting (10) Patent No.: US 11,503,989 B2
(45) Date of Patent: Nov. 22, 2022

(54) MULTI-CHANNEL SYSTEM

(71) Applicant: OPCOM INC., New Taipei (TW)

(72) Inventor: Chih-Yu Ting, New Taipei (TW)

(73) Assignee: OPCOM INC., New Taipei (TW)

( * ) Notice: Subject to any disclaimer, the term of this patent is extended or adjusted under 35 U.S.C. 154(b) by 178 days.

(21) Appl. No.: 16/879,868

(22) Filed: May 21, 2020

(65) Prior Publication Data
US 2021/0307596 A1 Oct. 7, 2021

Related U.S. Application Data

(60) Provisional application No. 63/003,307, filed on Apr. 1, 2020.

(51) Int. Cl.
| | | |
|---|---|---|
| A61B 1/00 | (2006.01) |
| A61B 1/012 | (2006.01) |
| A61B 1/018 | (2006.01) |
| A61B 1/015 | (2006.01) |
| A61B 1/05 | (2006.01) |
| A61B 1/005 | (2006.01) |
| A61B 1/06 | (2006.01) |
| A61M 25/00 | (2006.01) |
| A61B 17/00 | (2006.01) |
| A61B 17/34 | (2006.01) |
| A61B 17/32 | (2006.01) |
| A61B 17/29 | (2006.01) |

(52) U.S. Cl.
CPC ............ *A61B 1/012* (2013.01); *A61B 1/0052* (2013.01); *A61B 1/0057* (2013.01); *A61B 1/00096* (2013.01); *A61B 1/015* (2013.01); *A61B 1/018* (2013.01); *A61B 1/0125* (2013.01); *A61B 1/05* (2013.01); *A61B 1/0676* (2013.01); *A61B 17/29* (2013.01); *A61B 17/320016* (2013.01); *A61B 17/3478* (2013.01); *A61B 2017/0034* (2013.01); *A61B 2017/00358* (2013.01); *A61B 2217/005* (2013.01); *A61B 2217/007* (2013.01); *A61M 25/0026* (2013.01)

(58) Field of Classification Search
None
See application file for complete search history.

(56) References Cited

U.S. PATENT DOCUMENTS 5,201,908 A * 4/1993 Jones ................ A61B 1/12
600/125
5,674,182 A * 10/1997 Suzuki ................ A61B 1/121
600/129

(Continued)

*Primary Examiner* — Timothy J Neal
(74) *Attorney, Agent, or Firm* — Winston Hsu (57) ABSTRACT

Provided is an endoscope system including an elongated tube with one or more channels extending in a longitudinal direction along the elongated tube. The channels allow inserting of a viewing device for obtaining images from the distal end, inserting of surgical instruments to operate at the distal end, or passing of materials such as air or water. The channel for inserting the viewing device is enclosed or has a cover at the distal end of the elongated tube, such that the viewing device has no direct contact of body tissues, thereby eliminating the need for sterilization. Also provided is a safe and economical method for conducting endoscopy involving one-time use of a tube to keep the viewing device from directly contacting the body tissues.

14 Claims, 13 Drawing Sheets

(56) References Cited

U.S. PATENT DOCUMENTS

| | | | |
|---|---|---|---|
| 2006/0149131 A1* | 7/2006 | Or | A61B 1/00142 600/154 |
| 2007/0112336 A1* | 5/2007 | Aizenfeld | A61B 90/40 606/1 |
| 2010/0210905 A1* | 8/2010 | Takeuchi | A61B 1/00135 600/110 |
| 2013/0265798 A1* | 10/2013 | Kudo | G02B 23/2423 362/574 |
| 2015/0094611 A1* | 4/2015 | Farhadi | A61B 10/04 600/562 |
| 2015/0374211 A1* | 12/2015 | Smith | A61B 17/3421 600/114 |
| 2017/0265723 A1* | 9/2017 | Yamaya | A61B 1/018 |

* cited by examiner

MULTI-CHANNEL SYSTEM

BACKGROUND

1. Technical Field

The present disclosure relates to medical systems, in particular, an endoscope system comprising more than one channels for obtaining images and operating at the distal end inside a body cavity. The present disclosure also relates to methods for conducting endoscopy without direct contact between a viewing device and body tissue surfaces.

2. Description of Associated Art

Endoscopy is now a medical procedure routinely carried out for examining body cavities, including ducts and hollow organs. By means of an endoscope, endoscopy allows direct observation inside of body with minimal incision of the body. Current designs of endoscopes usually consist of a tube through which the optical information from the body interior is transmitted through. Other endoscopes have a CCD image-converter chip, which acts as a miniaturized TV camera and makes possible output on a monitor. Further, endoscopy also allows additional medical procedures such as removal of tissue portions for biopsy by means of introducible forceps, loops, irrigators and suction apparatus.

However, the viewing device of an endoscope making use of lens or miniaturized camera is a very expensive piece of equipment, and thus there is an economical reason to use endoscope repeatedly. Since endoscopes are used inside a body, its repeated use needs strict sterilization to avoid cross-contamination. Endoscopes that make contact with body tissues are dismantled after each use and thoroughly cleaned and sterilized. The procedures involved are cumbersome and time-consuming, and add to the maintaining cost of endoscopes. Furthermore, the need for endoscopes to undergo frequent cleaning and sterilizing procedures after each use substantially shorten the timespan of the product life.

Hence, an endoscopy system with lower operational cost while still allowing for a safe and sanitary medical procedure is highly sought after.

SUMMARY

In view of the foregoing, the present disclosure provides a multi-channel endoscope comprising an elongated tube, wherein one or more channels extends in the longitudinal direction in the lumen of the elongated tube. In an embodiment, the elongated tube comprises a channel for inserting a viewing device, where the distal end of the channel is enclosed or covered. Therefore, the elongated tube provides an airtight, germ-tight and watertight enclosure of the view device at the distal end and along the shaft of the viewing device. In another embodiment, the elongated tube provides further working channels for inserting of surgical instruments such as scalpel devices, forceps, loops, needles, irrigators, suction apparatus, or optical fibers such as laser fibers for operation. The term "scalpel device" used herein is not limited to the type or kind thereof. For example, the scalpel device may be an electrosurgical unit having a specific shape according to the function thereof, a bipolar scalpel, a harmonic scalpel, a tissue agglutination apparatus, or a laser. In a further embodiment, the elongated tube provides further channels for passing additional material, such as drugs, gases, air, fluid, solution, water or a combination thereof.

In one embodiment, at least one illuminating source is provided on the elongated tube. In another embodiment, at least one illuminating source is provided on the distal end of the elongated tube. In a further embodiment, an illuminating source is provided at the proximal end of the elongated tube and transmitted to the distal end of the elongated tube to provide light for the imaging device. In another embodiment, an illuminating source is located on the distal end of the elongated tube and separated from the closed channel of the elongated tube. In still another embodiment, the illuminating source is located away from the closed channel of the elongated tube.

In one embodiment, the distal end of the closed channel of the elongated tube for inserting viewing device is provided with a cover. In another embodiment, the cover is waterproof. In a further embodiment, the cover is transparent. In a further embodiment, the distal end of the closed channel of the elongated tube is enclosed integrally in one-piece. For example, the distal end of the closed channel of the elongated tube is enclosed integrally without an additional or removable cap covered thereon.

In one embodiment, the distal end of the closed channel for inserting the viewing device protrudes out of the end of the elongated tube. In other words, the distal end of the closed channel for inserting viewing device creates an overhang or protrusion at the distal end of the elongated tube.

In one embodiment, the multi-channel endoscope of the present disclosure further comprises a viewing device. The viewing device comprises an image module for taking optical image at the distal end of the viewing device. The viewing device is inserted into the closed channel of the elongated tube of the multi-channel endoscope. When inserted into the closed channel, the image module on the distal tip of the viewing device locates at a location further distal to the end of the elongated tube. In other words, the image module protrudes out of the distal end of the elongated tube. As such, the image module on the distal end of the viewing device is located at a position that is further distal to the illuminating source on the distal tip of the elongated tube so as to avoid formation of flares when acquiring images with the viewing device.

In one embodiment, the endoscope is further provided with a control device to control the bending, rotation, or curvature of the endoscope for surgical operations.

The elongated tube of the multi-channel endoscope can be one-time-use and disposable to avoid disinfection, thereby improve patient safety.

The viewing device of the multi-channel endoscope provided in this disclosure works without direct contact with human body and therefore can be used repeatedly without disinfection or sterilization and minimize contamination. Therefore, the present disclosure not only ensures patient safety but also reduces overall cost of carrying out an endoscopy.

In one embodiment, the elongated tube can be rigid, semi-rigid or flexible. In another embodiment, the viewing device can be rigid, semi-rigid or flexible. In a further embodiment, the elongated tube is provided with at least one linear rigid element extending along the longitudinal axis of the elongated tube to provide different rigidity and flexibility to the insert tube at different parts of the elongated tube. For example, the linear rigid element can be a metal wire, strip, or concentric cylinder with different lengths. The linear rigid element with different lengths provided in the elongated tube contributes to different levels of rigidity or flexibility of the elongated tube at different positions along the longitudinal axis of the elongated tube.

The multi-channel endoscope operates in different curvatures or bending direction, including but not limited to one-directional rotation, two-directional rotation or four-directional rotation.

BRIEF DESCRIPTION OF THE DRAWINGS

FIGS. 11A to 11C show the comparison of light reflection on the image obtained by the viewing device with different locations of the illuminating source. FIG. 11C presents a clearer image with less flare or light reflection.

DETAILED DESCRIPTION OF EMBODIMENTS

The present disclosure provides a channel endoscope comprising a removable viewing device and an elongated tube. A closed channel with a closed distal end allowing insertion of a viewing device, a working channel for inserting a surgical instrument, and at least one channel for inserting tubes that are commonly used in endoscopy are provided inside the lumen of the elongated tube. The channels of the elongated tube may include a water/air inlet channel, a drainage channel, an illuminating source channel, a channel for a linear controlling unit (e.g., a wire) to control the bending or rotation of the distal end of the elongated tube or a drug delivery channel. The elongated tube is connected to a handle part. The handle part provides a control device, which controls the bending part at the distal end of the elongated tube to make different degrees of bending, so as to perform any actions required during an endoscopy procedure.

The handle part connected to the elongated tube has a control device to control the bending of the distal end of the elongated tube so as to make different degrees and angles of bending. In one embodiment, the control device may be a rocker rod or a rotating handle. In another embodiment, the control device is a bending bar. The control device is connected to the distal end of the elongated tube with a linear controlling unit.

The elongated tube comprises a closed channel, a working channel, a water inlet, a drainage channel and a drug delivery channel in its lumen. The elongated tube may further include at least one illuminating source at the distal end, and the proximal end of the elongated tube is connected to the handle part comprising the control device. One or more sockets may be arranged on the side wall of the handle part, and each socket may be connected to at least one channel.

In the endoscope system of the present disclosure, at least a portion of the viewing device is a rigid tube, or a combination of flexible and rigid materials. In an embodiment, the handle part connected to the elongated tube is provided with a first socket for inserting the viewing device, a second socket connected to the working channel, a third socket connected to the air supply channel, and a fourth socket for the water supply channel. The positions of the sockets on the handle part are not limited, as long as they do not interfere with the prescribed functions of the sockets and the handle part. For example, the viewing device socket is connected to and in communication with the closed channel for inserting the viewing device; the instrument socket is connected to and in communication with the working channel; the air supply socket is connected to and in communication with the air supply channel; the water supply socket is connected to and in communication with the water supply channel; and the wire supplying power to the illuminating source is connected to the socket for the viewing device. In an embodiment of the present disclosure, the viewing device socket that connects to the closed channel for inserting the viewing device is configured at the proximal end of the handle part, away from the elongated tube. The sockets may be further connected to, or mounted with, a protective cover or sheath that extends from the opening of the sockets towards the operator. The protective cover or sheath thereby provides a barrier between the devices inserted into the elongated tube through the sockets, for example, a viewing device inserted into the closed channel of the elongated tube, and the subject receiving endoscopy, and can further protect the viewing device from being contaminated.

The elongated tube is a flexible tube, and the viewing device tube for a viewing device is also a flexible tube; the side wall of the handle part connected to the elongated tube is provided with a viewing device socket and an instrument socket. The viewing device socket is connected to and in communication with the closed channel, and the instrument socket is connected to and in communication with the working channel.

Toward the distal end of the elongated tube, a bending part capable of bending is configured. On the sidewall of the handle part connected to the elongated tube, a control device is provided for driving the bending. In one embodiment, the control device includes a rotary handle that rotates in one, two or four directions and bends the distal end of the elongated tube in one, two or four directions, respectively. In another embodiment, the control device includes a bending bar that may be pushed forward or backward to bend the distal end of the elongated tube in one, two or four directions, respectively.

In an embodiment, the illuminating source is configured at the distal end of the elongated tube. In another embodiment, the illuminating source is configured on the distal tip of the elongated tube. The illuminating source is thereby configured to locate separately from the viewing device, and away from the image module on the distal end of the viewing device. This placement of the illuminating source away from the image module avoids flares and forms clearer images. In addition, the illuminating source locating outside of the closed channel means that the illuminating source is able to provide light without a cover, and therefore avoids light reflection in the image captured by the image module of the viewing device inserted in the closed channel. Moreover, the illuminating source's location on the elongated tube and not on the viewing device has further advantage in that the bigger cross-sectional area of the elongated tube than the viewing device provides better dissipation of heat produced by the illuminating source. As such, because the illuminating source is now located away from the image module and has more room to dissipate the heat produced, the image sensor in the image module, which is heat-sensitive, will be less affected by the heat produced by the illuminating source. On the other hand, by placing the illuminating source on the distal end of the elongated tube, an illuminating source with greater brightness can be used to improve the resolution of images. Also, more illuminating sources can be used since there is more room on the distal end of the elongated tubes.

The distal end of the closed channel for inserting a viewing device is provided with a waterproof transparent cover. The closed channel is configured to enclose with a distal end that protrudes out of the distal end of the elongated tube. The distal end of the viewing device, when inserted into the closed channel, therefore can reach to the protruding distal end and carry out its function at a further distal location than the illuminating source. This configuration of the viewing device, on the distal end of which an image module is configured, and the illuminating source locating at different distal positions avoids formation of flares when acquiring images with the viewing device.

The distal end of the viewing device is equipped with an image module that integrates all imaging devices. The image module is connected with a data cable that leads from the distal end of the viewing device to the proximal end of the viewing device to connect to the display device. In an embodiment, the viewing device has a gap between the side of the viewing device and the sidewall of the closed channel. The gap allows air to pass and enables easy insertion of the viewing device into the closed channel, by avoiding possible formation of vacuum. In another embodiment, the sidewall of the closed channel is in a wave shape, such that at least one gap forms between the side of the viewing device and the sidewall of the closed channel when the viewing device is inserted into the closed channel.

In the present disclosure, the disposable elongated tube is used as a carrier or protection cover for the viewing device and surgical instruments, by providing an enclosed channel for inserting the viewing device and a working channel for inserting surgical instruments. The viewing device has no direct contact with body tissues. Therefore, it is no longer needed to clean and disinfect or sterilize the viewing device. Furthermore, with the disposable use of the elongated tube, the chance of cross contamination due to insufficient disinfection is also minimized. In addition, if the disposable elongated tube is a flexible tube or a combination of flexible and rigid materials, a bending part is provided on the distal end, and at least one side of the handle part is also provided with a rotating handle to control the bending part and achieve one or two-way rotation. With the rotating handle, the operator only needs to use the rotating handle of the elongated tube to achieve the corresponding steering action of the elongated tube. The distal end of the viewing device and surgical instrument inserted into the channels of the elongated tube can thereby be bended to the required position under the control of the rotating handle of the handle part of the disposable elongated tube, facilitating the operator to carry out various medical procedures.

Therefore, the multi-channel endoscope of the present disclosure has a simple structure that facilitates easy operation and exempts sterilization of the viewing device.

As used herein, the term "viewing device" refers to any device that comprises lenses or cameras that obtain a visual image at one end and transmit to the other end of the viewing device. For example, the viewing device may be a visual image tube with an image module mounted on one end of the tube, obtains a visual image through the image module, transmits the visual image through the tube, and shows the visual image on a video monitor on the other end of the visual image tube.

As used herein, the term "elongated" is not meant to limit the device to any particular dimensions, but merely to indicate that the device has a length that generally exceeds its diameter, such as a tube-like structure, and the device of the present disclosure encompasses all embodiments employing a means comprising lumen allowing at least one channel to be formed in the lumen through which a viewing device or other instruments can be inserted. As such, the elongated tube as used herein may be an insert tube that is inserted into the body cavity to carry out endoscopy.

As used herein, the terms "distal end" and "proximal end" refer to the ends of a structure that are closer and farther from the treatment zone, respectively. For instance, as compared with the proximal end of the elongated tube, the distal end of the elongated tube is closer to the surgical site of the patient.

The present disclosure will be further described in detail with reference to the accompanying drawings and embodiments below.

Figure 1:
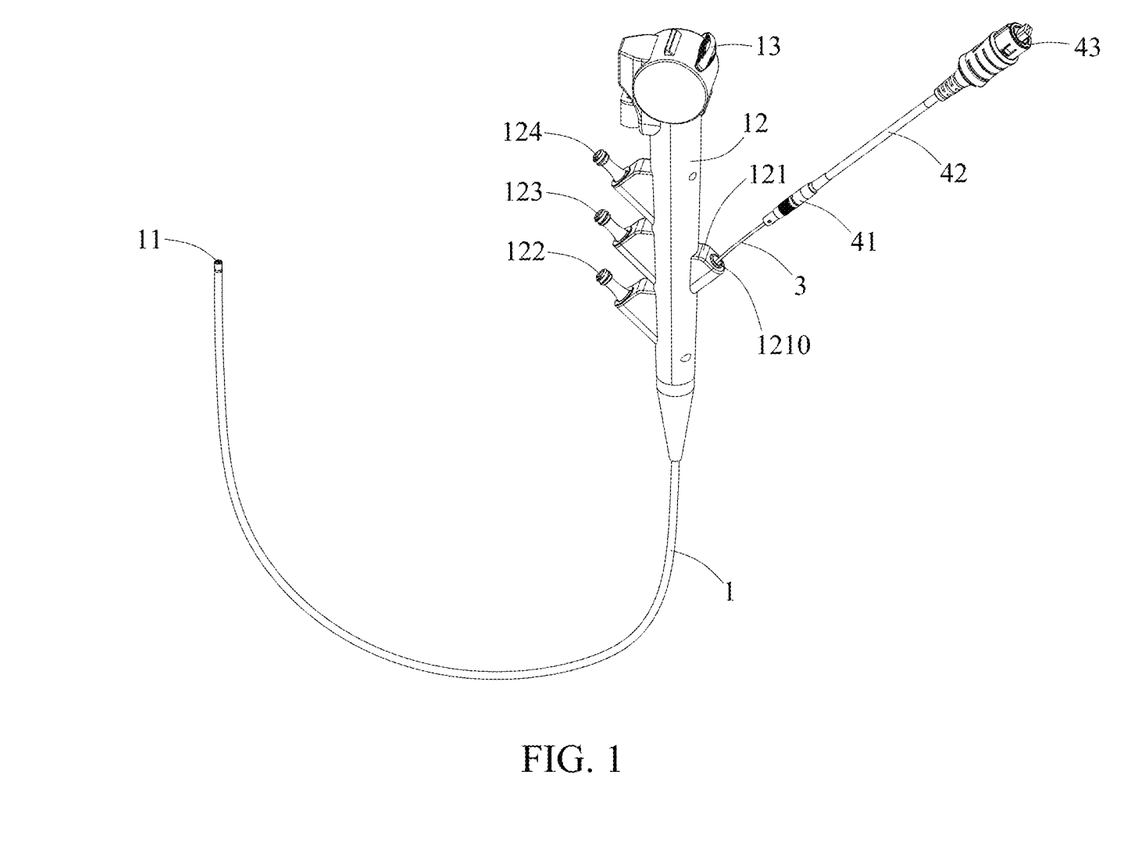
FIG. 1 is a perspective view of a three-dimensional structure of a disposable elongated tube (a rigid tube to insert into body) and a viewing device (with a rigid tube as the shaft portion) inserted into the elongated tube, according to the first embodiment of the present invention.
Figure 2:
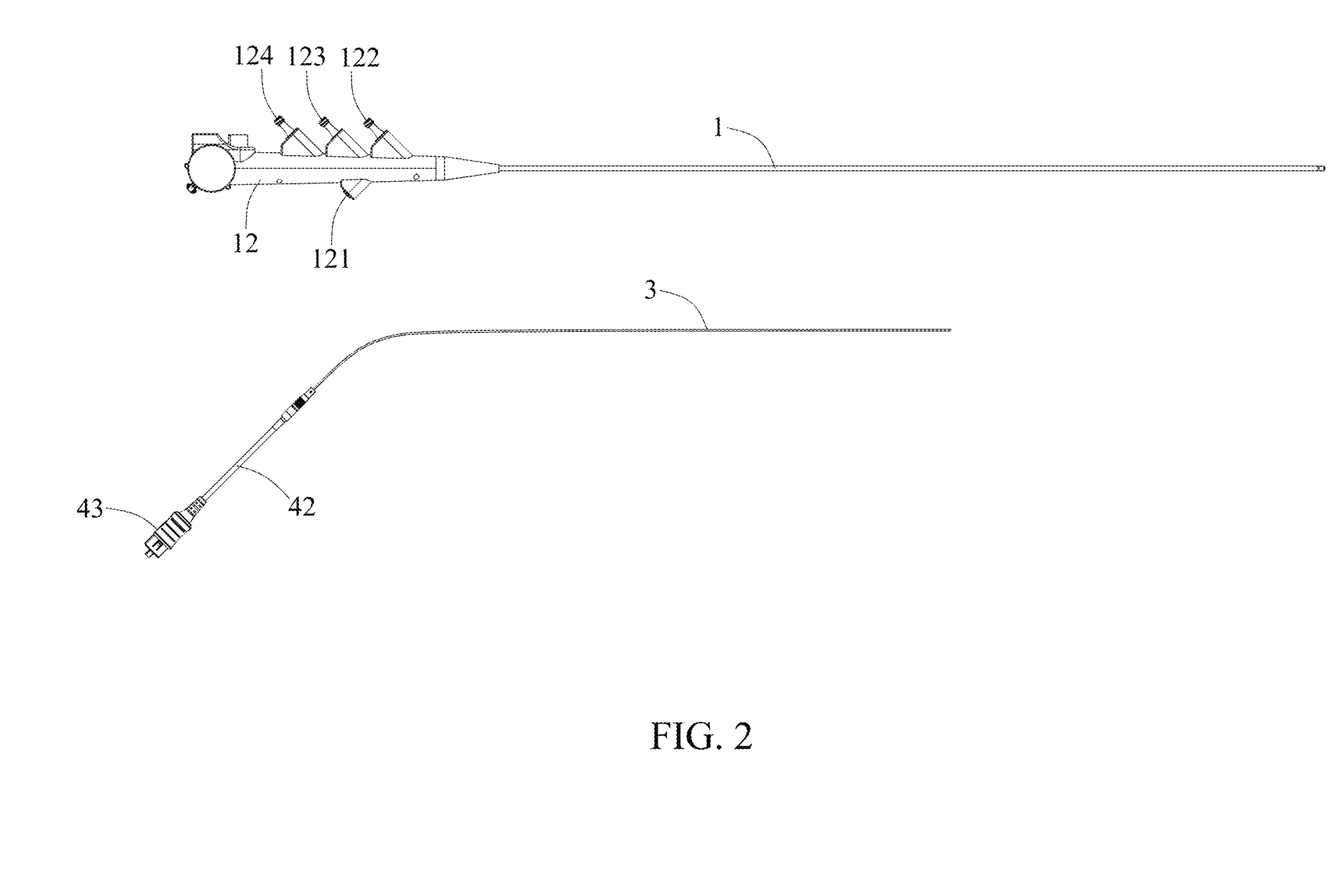
FIG. 2 is a front side view of the disposable elongated tube 1 and a viewing device 3 in a tubular form of the present invention according to the first embodiment.
Figure 3:
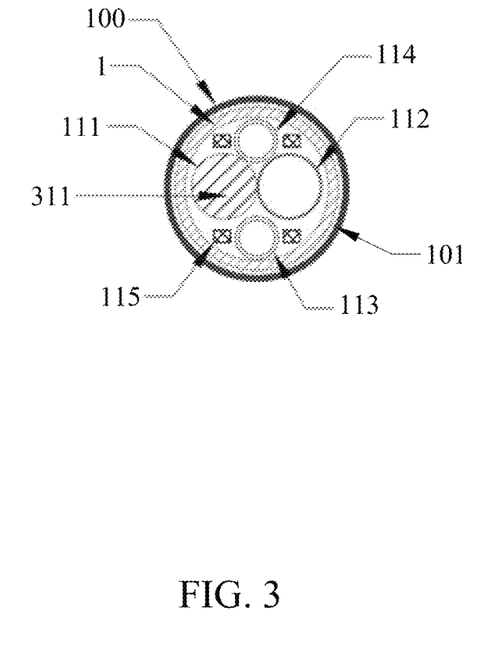
FIG. 3 is a front view of the distal end of the elongated tube.

For the first embodiment, please refer to FIG. 1, FIG. 2 and FIG. 3. First of all, FIG. 1 provides a schematic overview of the entire endoscopy system of the present disclosure, including a bending bar 13 that controls bending of a distal end 11 of an elongated tube 1. The elongated tube 1 is connected to a handle part 12, and the handle part 12 are disposed with a socket connecting to an air channel 122, a socket connecting to a water channel 123, a socket connecting to a working channel 124, and a socket 121 connecting to a closed channel for inserting of the viewing device 3. The socket 121 is configured with a female connector 1210 where a viewing device 3 having a male connector 41 inserts into and docks on. In an embodiment, the viewing device 3 is in the form of a visual image tube. The viewing device 3 has a camera control unit (CCU) connector 43 that connects to CCU, and a data cable 42 that extends the length of the visual image tube to transmit the image data from the distal end to the connector 43.

Referring to FIG. 2, a multi-channel endoscope according to the present disclosure includes a removable viewing device 3 and a disposable elongated tube 1. The distal end of the removable viewing device 3 is provided with an image module (not shown) integrating all imaging devices. The image module is connected with a data cable 42, and the data cable 42 leads from the distal end of the removable viewing device 3 to the proximal end thereof and is connected to a connector 43. The connector 43 then connects to a CCU (not shown). The disposable elongated tube 1 is connected to a handle part 12 provided with four channel sockets 121, 122, 123, 124.

FIG. 3 shows the front view of the distal end of a disposable elongated tube. The disposable elongated tube 1 is provided along its lumen with a closed channel 111 where the distal end is closed and into which a viewing device can be inserted; a working channel 112 for inserting a surgical instrument; and a plurality of additional channels for inserting the feeding tubes commonly used with endoscopes, for example, an air supply channel 113 for an air supply tube, a water supply channel 114 for a water supply tube, and a plurality of illuminating sources 115.

Figure 4:
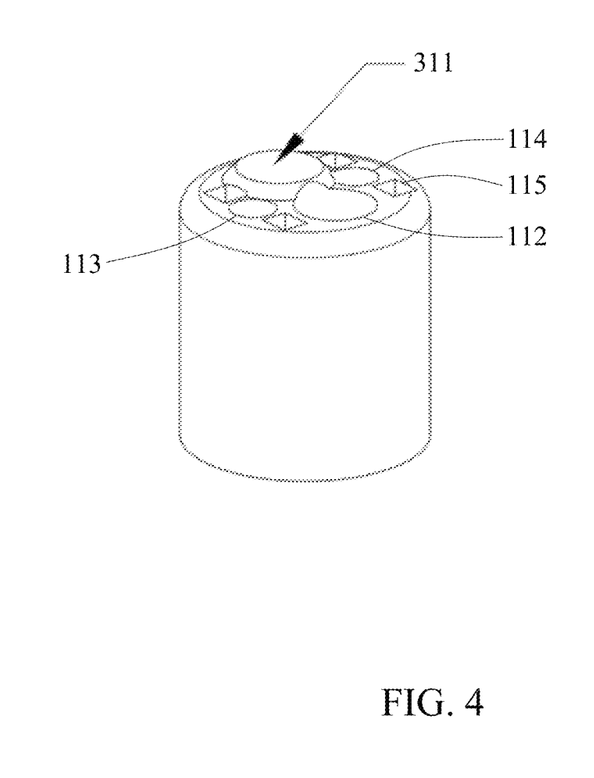
FIG. 4 is a 3-dimensional view of the distal end of the elongated tube.

Referring now to FIGS. 2 to 4, the closed channel 111, the working channel 112, the air supply channel 113 and the water supply channel 114 are configured to extend longitudinally inside the lumen of the elongated tube 1 covered by the first covering unit 101 and/or the second covering unit 100, and the illuminating sources 115 are disposed at the distal end of the elongated tube 1. The first covering unit 101 may be configured to cover at least a part of the outer surface of the elongated tube 1 so as to increase the coaxiality, curvature, and/or extensibility of the elongated tube 1 during operation such as bending or rotating. In one embodiment, the first covering unit 101 is a net-like body braided on the outer surface of the elongated tube 1, and the net-like body is formed by fibers of a metal-containing material such as a stainless steel material, a resin material, a silicone material, or a combination thereof. The second covering unit 100 may be configured to cover the first covering unit 101 and/or at least a part of the outer surface of the elongated tube 1 so as to prevent the first covering unit 101 and/or the outer surface of the elongated tube 1 from directly contacting the patient's body cavity, thereby ensuring the safety of the patient. In one embodiment, the second covering unit 101 may be a tube, a sleeve, a sheath, or a membrane that is made of a plastic material such as a heat shrink plastic or a silicone material. The proximal end of the disposable elongated tube 1 is provided with a handle part 12, and side walls of the handle part 12 are provided with four channel sockets 121, 122, 123, 124. The four channel sockets 121, 122, 123, 124 are respectively connected with the viewing device channel 111, the working channel 112, the air supply channel 113, and the water supply channel 114, such as the arrangement with the viewing device socket 121 connected to the viewing device channel 111, the working channel socket 122 connected to the working channel 112, the air supply socket 123 connected to the air supply channel 113, and the water supply socket 124 connected to the water supply channel 114. The viewing device socket 121 may also be used to connect to the illuminating sources 115. The distal end of the viewing device channel 111 is provided with a transparent waterproof cover 311 to form a closed channel.

In the multi-channel endoscope according to the present disclosure, when in use, the viewing device 3 and the surgical instrument are inserted into the viewing device socket 121 and the instrument socket 122, respectively, at the handle part 12 connected to the proximal end of the elongated tube 1, and the sockets are in turn connected to the closed channel 111 and the working channel 112, respectively. The air supply socket 123 and water supply socket 124 are respectively connected with the air supply channel 113 and the water supply channel 114. Upon necessary, the water inlet tube, the air inlet tube, the draining tube, the guide light (e.g., optional LED light or fiber optic light), the drug delivery tube, etc. may be simultaneously inserted into the corresponding channel sockets. Therefore, using the elongated tube 1 of the present disclosure can achieve multiple medical procedures in addition to providing a visual image at the distal end that is inserted into the body cavity of a patient.

Referring to FIG. 3, because the distal end of the closed channel 111 for inserting the viewing device 3 is equipped with a waterproof cover 311 that encloses the entire channel, after completion of the operation, the viewing device 3 do not need to be cleaned or sterilized as it does not make contact with body tissues, such that the cross-contamination or cross-infection of the patient due to incomplete disinfection of the viewing device 3 can be avoided. As shown in FIG. 4, which is a 3-dimensional view of the distal end of the elongated tube, the enclosed end 311 of the channel for the viewing device protrudes out of the distal end of the elongated tube. The illuminating sources 115 are configured on the distal tip of the elongated tube, separated from the viewing device, and located outside of the channel for the viewing device.

Figure 5:
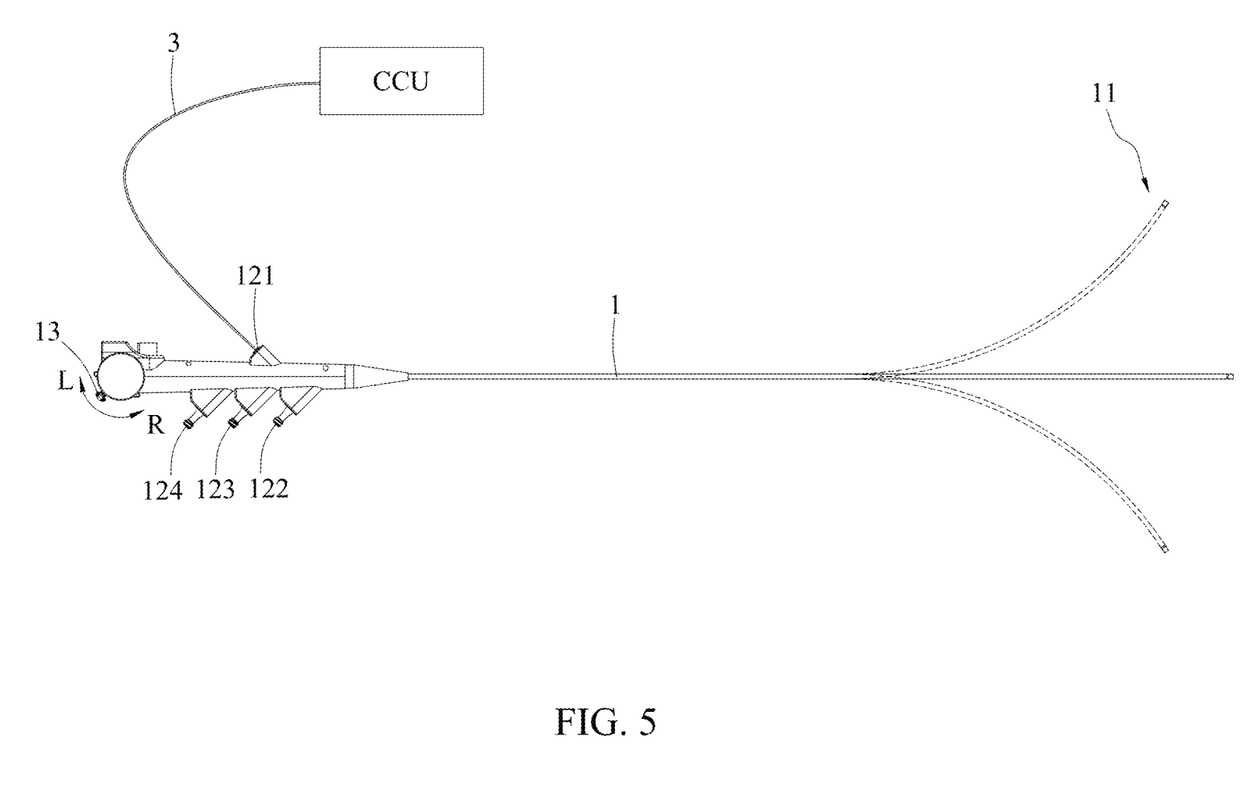
FIG. 5 is a schematic diagram of a state of use of the present invention according to the second embodiment.

As shown in FIG. 5, the present disclosure provides a second embodiment of the multi-channel endoscope. The difference of this embodiment from the first embodiment is that the disposable elongated tube 1 is a flexible tube or a combination of flexible and rigid tubes, while the viewing device 3 inserted into the elongated tube 1 through the viewing device socket 121 is a flexible tube. The bending bar 13 is used to control the bending at the distal end 11 of the elongated tube 1 toward a predefined direction, e.g., bending to the right (R) or left (L). The viewing device 3 is connected to a camera control unit (CCU).

Figure 6:
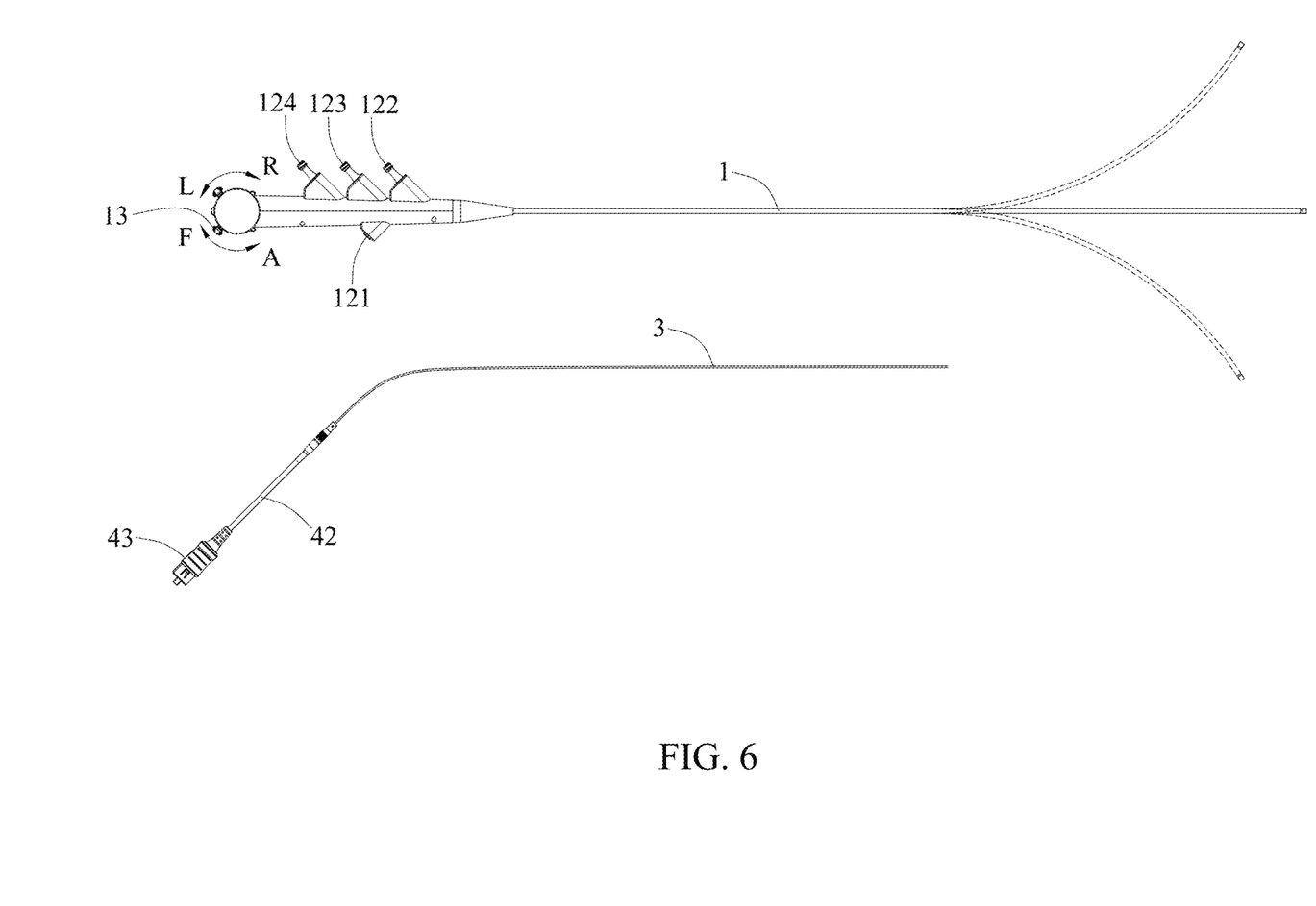
FIG. 6 is a schematic diagram of the structure of the disposable elongated tube (a flexible tube or a combination of rigid and flexible tube) and the viewing device (a flexible tube) according to the third embodiment.
Figure 7:
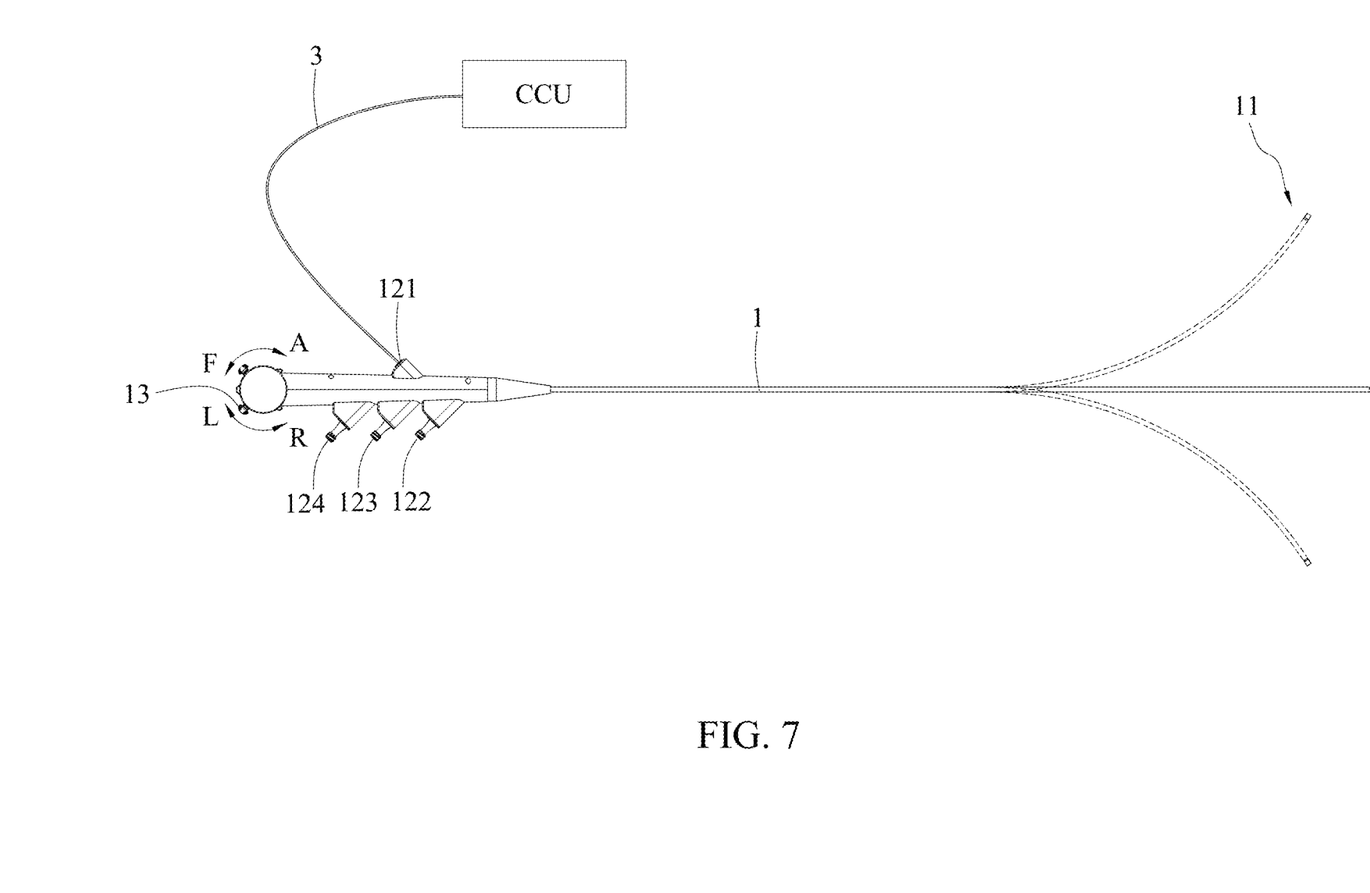
FIG. 7 is a schematic diagram of a use state of the present disclosure in the fourth embodiment.

FIGS. 6 and 7 show the third and fourth embodiments of the channel endoscope according to the present disclosure. A portion of the viewing device 3 in the third embodiment shown in FIG. 6 is a rigid tube. In the fourth embodiment shown in FIG. 7, the viewing device 3 is a flexible tube. The difference of the third and fourth embodiments from the second embodiment is that the disposable elongated tube 1 is provided with two bending bars 13, and each bending bar controls and bends the bending part of the disposable elongated tube 1 at the distal end to achieve two-directional bending, e.g., bending to the right (R) or left (L) directions with one bending bar and bending to two other directions (F) and (A) that are in 90 degrees to the (R) and (L) directions with another bending bar, such that the bending part of the disposable elongated tube 1 can achieve a total of four-directional bending.

Figure 8:
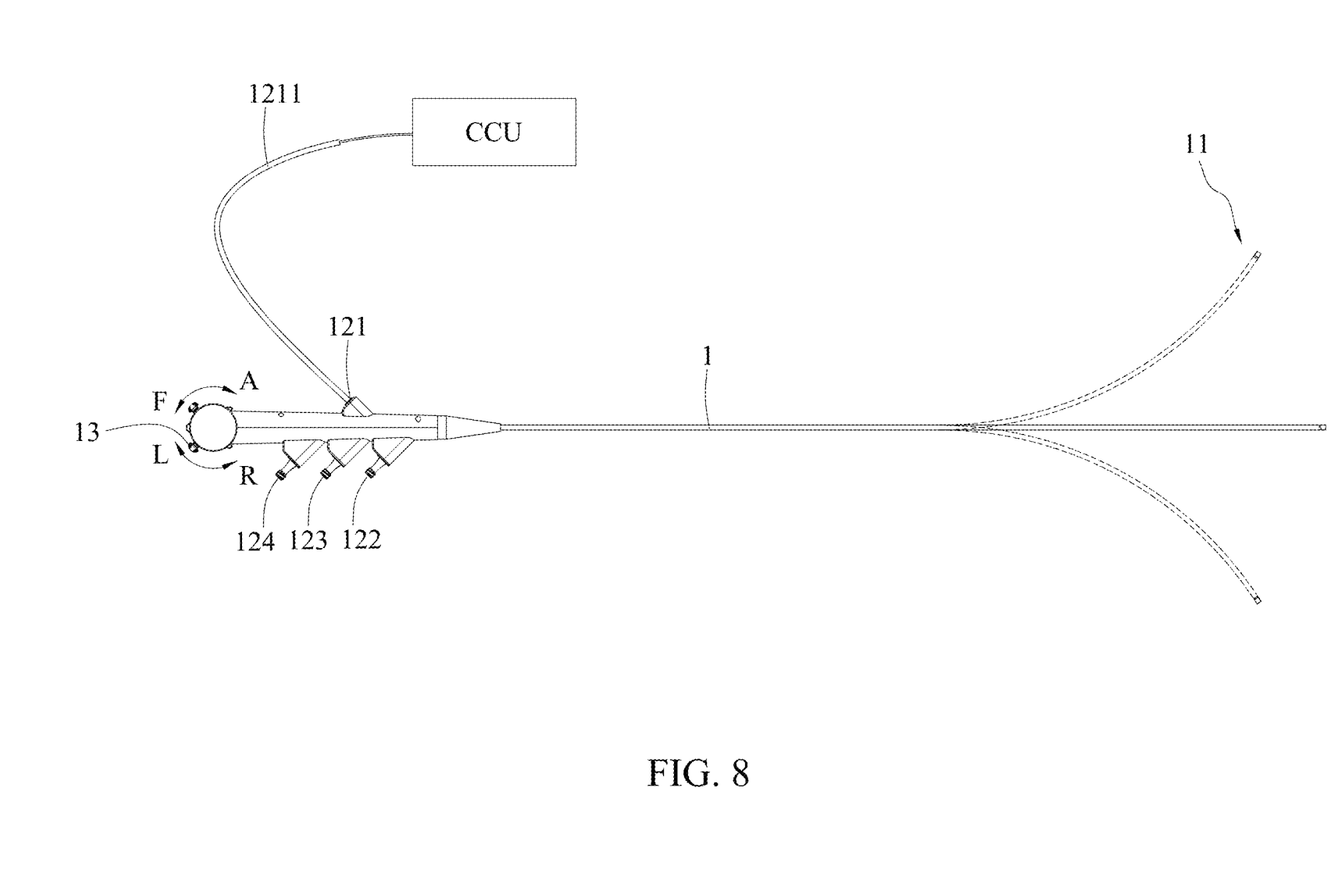
FIG. 8 is a schematic diagram of a use state of the present disclosure according to an embodiment, where the socket for inserting the viewing device is coupled with a sheath.

FIG. 8 shows another embodiment where an opening of the viewing device socket 121 is coupled with a sheath 1211. The sheath 1211 is an elongated sleeve with openings at two ends. The sheath 1211 couples to the opening of the viewing device socket 121 to encircle the circumference of the socket opening. The other end of the sheath 1211 allows inserting of a viewing device. The viewing device socket 121 coupled with a sheath 1211 provides extended protection of the viewing device 3 from being in contact with the body tissues or bodily fluid from the body tissues.

Figure 9:
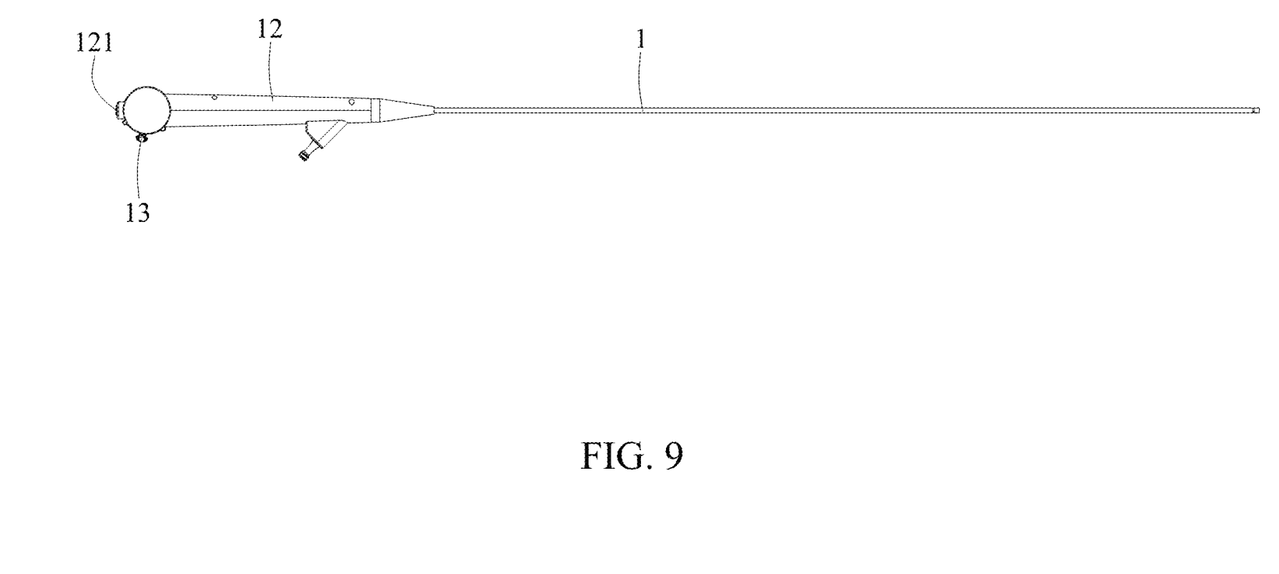
FIG. 9 is a schematic diagram of a use state of the present disclosure to an embodiment, where the socket for inserting the viewing device is configured at the proximal end of the handle part.

The positions of sockets on the handle part 12 are not limited and can be configured according to user's needs. For example, in an embodiment as shown in FIG. 9, the viewing device socket 121 is located at the proximal end of the handle part 12, at a farthest distance from the elongated tube 1 to reduce the risk of the viewing device 3 being contaminated by the body tissues or bodily fluid from the body tissues.

Figure 10:
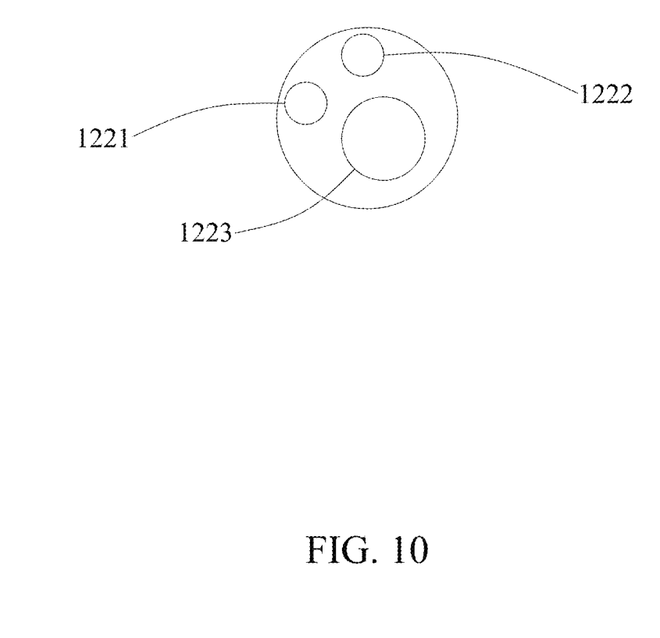
FIG. 10 is a cross-sectional diagram of the socket disposed on the handle of the endoscopy system and connects to the channel for inserting the viewing device.

FIG. 10 shows a socket structure for the viewing device channel on the handle part connected to the elongated tube. The socket contains a viewing device channel 1223. The tip of the channel is a closed structure. The other two conductive pads 1221 and 1222 connect power for the illuminating source disposed at the distal end of the elongated tube. The illuminating source is thereby electrically powered when the viewing device is inserted into the viewing device channel through the socket. The viewing device contains the power supply for the elongated tube. The elongated tube before insertion of the viewing device is therefore free of electric power. Such configuration of an elongated tube without electric power component allows a simpler and easier manufacturing and also better compliance to regulation governing medical devices.

Figure 11A:
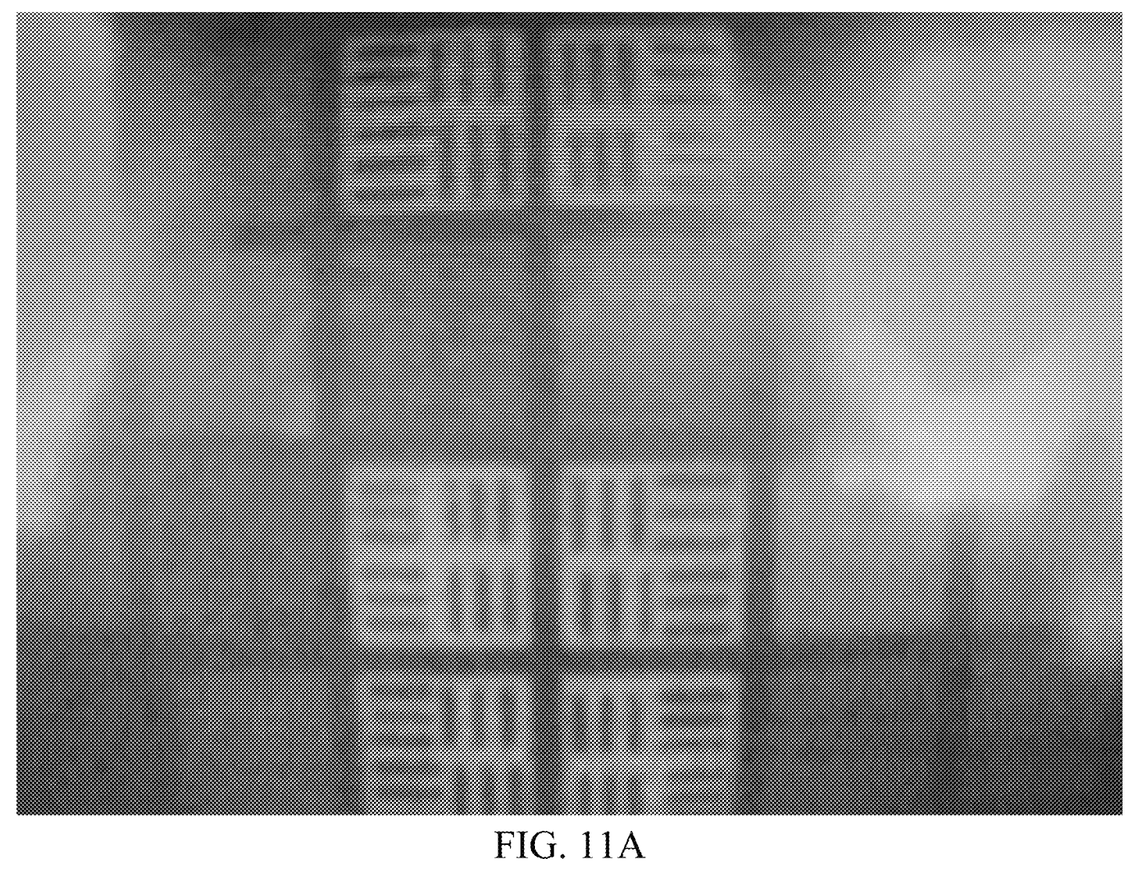
FIGS. 11A and 11B show the image obtained by the image module integrated with the illuminating source at the distal end of the viewing device in the closed channel. By contrast.
Figure 11B:
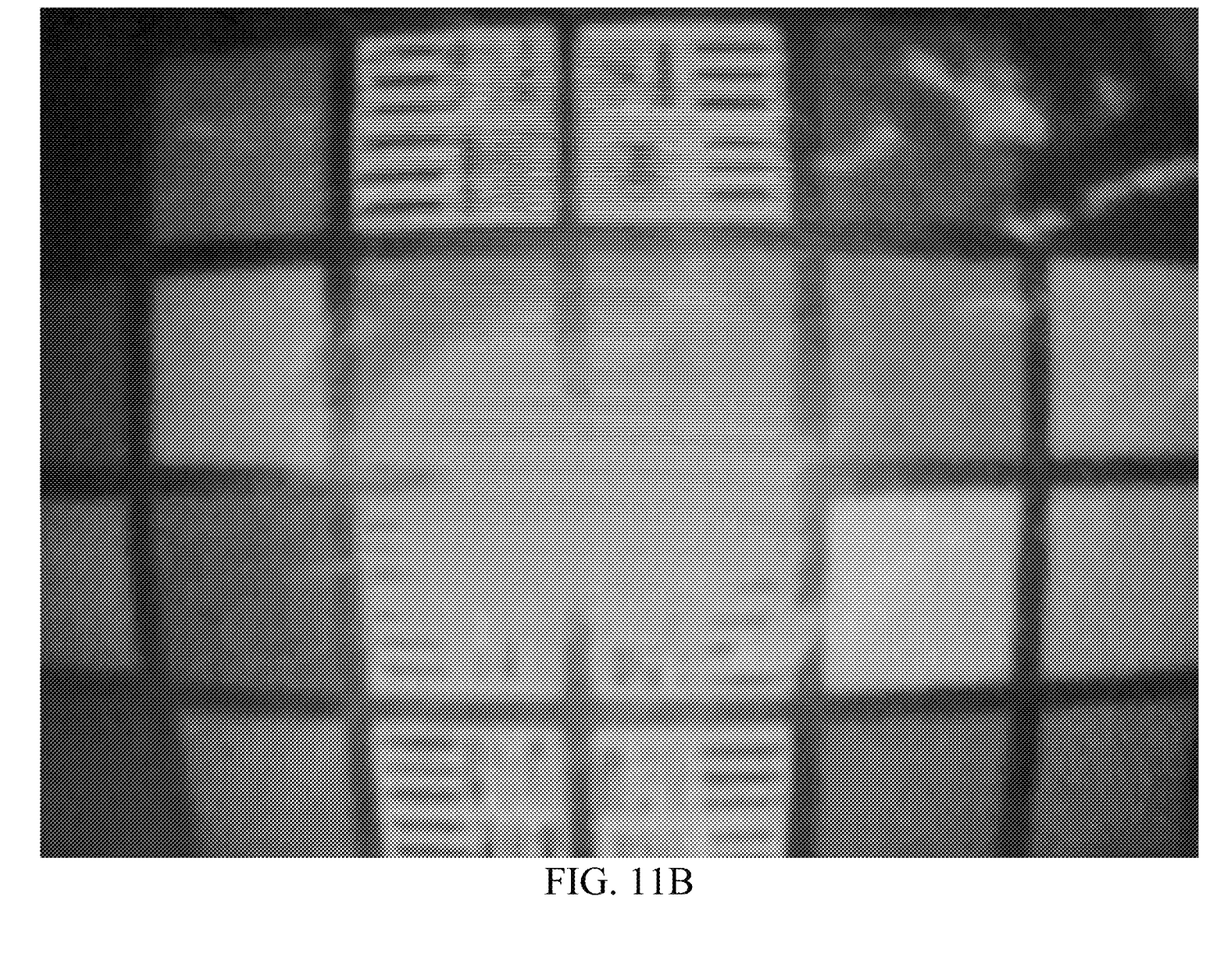
Figure 11C:
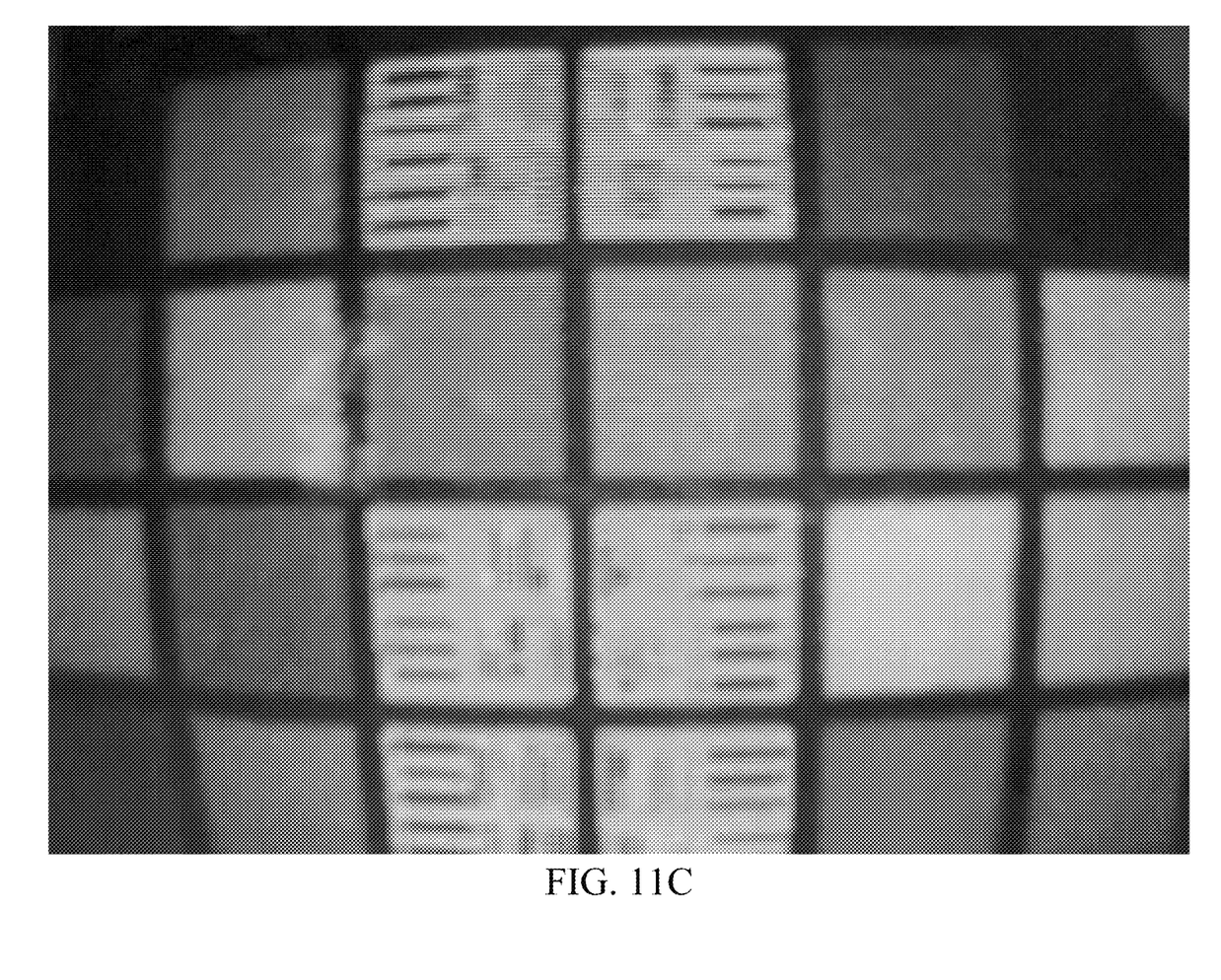
FIG. 11C shows the image obtained by the image module at the distal end of the viewing device in the closed channel, where the illuminating source is located on the distal end of the elongated tube that are separated from the viewing device and/or the closed channel for inserting the viewing device. Compared to FIGS. 11A and 11B.

In the example of FIGS. 11A and 11B, the illuminating source is integrated with the image module and provided on the distal end of the viewing device. However, since the channel for inserting the viewing device is enclosed with a transparent cover, the light originating from the illuminating source and passing through the transparent cover usually lead to flares as shown in FIG. 11A, and light reflection as shown in FIG. 11B, in the image obtained. By contrast, in the embodiments of the present disclosure, at least one illuminating source is provided on the distal end of the elongated tube and is separated from the viewing device, the image module, and/or the closed channel for inserting the viewing device. This arrangement effectively avoids flares and light reflection produced by the cover of the closed channel and thus forms a clearer image, as shown in FIG. 11C.

Accordingly, the multi-channel endoscope of the present disclosure has a simple structure that facilitates easy operation, and its design with an elongated tube enclosing the viewing device eliminates the need of sterilization of the viewing device, and solves the problem of cross contamination or infection caused by repeated use, thereby improving the safety of patients receiving the endoscopy procedure and lowering the cost of such operation.

The above embodiments are only used to further describe a multi-channel endoscope of the present disclosure, but the present disclosure is not limited to the embodiments. Any simple modification to the above embodiments based on the technical essence of the present disclosure, equivalent changes and modifications all fall within the protection scope of the present disclosure.

What is claimed is:

1. An endoscope system comprising:
an elongated tube having a lumen and at least one channel extending in a longitudinal direction in the lumen of the elongated tube, with one of the at least one channel having a closed end at a distal end of the elongated tube;
an illuminating source provided on the elongated tube; and
a viewing device inserted into the one of the at least one channel having the closed end at the distal end of the elongated tube;
a handle part connected to a proximal end of the elongated tube;
at least one socket disposed on a side wall or a proximal end of the handle part, the at least one socket being connected to the one of the at least one the channel, the at least one socket connecting to the one of the at least one channel inserted with the viewing device comprising a conductive pad configured for connecting electrical power to the illuminating source at the distal end of the elongated tube.

2. The endoscope system according to claim 1, wherein the illuminating source is provided on the distal end of the elongated tube.

3. The endoscope system according to claim 1, wherein the elongated tube comprises a plurality of channels, and one of the plurality of channels is a working channel for insertion of a surgical instrument.

4. The endoscope system according to claim 3, wherein the surgical instrument is selected from the group consisting of a scalpel device, a forceps, a loop, a needle, an irrigator, and a suction apparatus.

5. The endoscope system according to claim 1, wherein the elongated tube comprises a plurality of channels, and one of the plurality of channels is a channel for passage of a material.

6. The endoscope system according to claim 5, wherein the material includes gases, air, fluid, drug, or a combination thereof.

7. The endoscope system according to claim 1, wherein the closed end of the one of the at least one channel inserted with the viewing device is transparent.

8. The endoscope system according to claim 1, wherein the closed end of the one of the at least one channel inserted with the viewing device protrudes out from the distal end of the elongated tube.

9. The endoscope system according to claim 1, wherein the viewing device comprises an image module configured for taking an optical image at a distal end of the elongated tube.

10. The endoscope system according to claim 1, further comprising a sheath coupled to the at least one socket.

11. The endoscope system according to claim 1, wherein the at least one socket connecting to the one of the at least one channel inserted with the viewing device is disposed on the proximal end of the handle part.

12. The endoscope system according to claim 1, wherein the handle part further comprises a control device configured for controlling bending or rotation at the distal end of the elongated tube.

13. The endoscope system according to claim 12, wherein the control device is configured to bend or rotate the distal end of the elongated tube in one direction, in two directions or in four directions.

14. The endoscope system according to claim 1, further comprising:
a sheath, wherein:
the illuminating source is provided on the distal end of the elongated tube;
the closed end of the one of the at least one channel inserted with the viewing device protrudes out from the distal end of the elongated tube; and
the at least one socket connecting to the one of the at least one channel inserted with the viewing device is disposed on the proximal end of the handle part and coupled to the sheath.

* * * * *